US005547929A

United States Patent [19]

Anderson, Jr. et al.

[11] Patent Number: 5,547,929
[45] Date of Patent: Aug. 20, 1996

[54] INSULIN ANALOG FORMULATIONS

[75] Inventors: James H. Anderson, Jr., Carmel; Michael R. De Felippis, Indianapolis; Bruce H. Frank, Indianapolis; Henry A. Havel, Indianapolis, all of Ind.

[73] Assignee: Eli Lilly and Company, Indianapolis, Ind.

[21] Appl. No.: 304,070

[22] Filed: Sep. 12, 1994

[51] Int. Cl.⁶ .................................................. A61K 38/28
[52] U.S. Cl. ............................ 514/3; 514/4; 530/303; 530/304; 530/305
[58] Field of Search ............................ 530/303, 304, 530/305; 514/3, 4

[56] References Cited

U.S. PATENT DOCUMENTS

| | | | |
|---|---|---|---|
| 2,799,622 | 7/1957 | Schlichtkrull et al. | 167/75 |
| 2,819,999 | 1/1958 | Schlichtkrul et al. | 167/75 |
| 2,836,542 | 5/1958 | Peterson et al. | 167/75 |
| 2,882,203 | 4/1959 | Peterson et al. | 167/75 |
| 3,060,093 | 10/1962 | Poulsen et al. | 167/75 |
| 3,937,820 | 2/1976 | Mager et al. | 424/178 |
| 4,608,364 | 8/1986 | Grau et al. | 514/4 |
| 4,959,351 | 9/1990 | Grau et al. | 514/4 |
| 5,028,587 | 7/1991 | Döschug et al. | 514/3 |
| 5,149,777 | 9/1992 | Hansen et al. | 530/303 |
| 5,164,366 | 11/1992 | Balschmidt et al. | 514/3 |
| 5,461,031 | 10/1995 | De Felippis | 514/4 |
| 5,474,978 | 12/1995 | Bakaysa et al. | 514/4 |

FOREIGN PATENT DOCUMENTS

| | | | |
|---|---|---|---|
| 0214826 | 3/1987 | European Pat. Off. | C07K 7/10 |
| 0375437 | 6/1990 | European Pat. Off. | |
| 0383472 | 8/1990 | European Pat. Off. | C07K 7/40 |
| 889769 | 2/1962 | United Kingdom | 81/1 |
| WO90/07522 | 7/1990 | WIPO | C07K 7/40 |
| WO95/00550 | 6/1995 | WIPO | C07K 7/40 |

OTHER PUBLICATIONS

Jens Brange, *Galenics of Insulin*, 32–42 (1987).
D. Brems et al., *Protein Engineering* 5(6): 527–33 (1992).
Protocol F32–MC–IOAI, Lilly Research Laboratories, Indianapolis, IN–Clinical Trial, Oct., 1993–Mar., 1994.
J. A. Galloway et al., *Diabetes Care* 5(suppl. 2): 13–22, Nov.–Dec. (1982).
J. A. Galloway et al., *Insulin Update*, 111–119 (1982).
B. Roy et al., *Journal of Clinical Endocrinology and Metabolism* 50(3):475–479 (1980).
M. Burge et al., *Clinical Research* 42(1):17A (1994).

*Primary Examiner*—Christine M. Nucker
*Assistant Examiner*—Benet Prickril
*Attorney, Agent, or Firm*—Steven P. Caltrider; David E. Boone

[57] ABSTRACT

The present invention discloses various parenteral pharmaceutical formulations, which comprise a mixture of a monomeric insulin analog and insulin-NPH. The analog formulations provide a rapid onset and a prolonged duration of action.

15 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Ile  Val  Glu  Gln  Cys  Cys  Thr  Ser  Ile  Cys  Ser  Leu  Tyr  Gln  Leu
 1                   5                        10                       15

Glu  Asn  Tyr  Cys  Asn
                20
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 28
        ( D ) OTHER INFORMATION: /note="Xaa at position 28 of SEQ
            ID NO:2 is Asp, Lys, Leu, Val, or Ala."

( i x ) FEATURE:
        ( A ) NAME/KEY: Modified-site
        ( B ) LOCATION: 29
        ( D ) OTHER INFORMATION: /note="Xaa at position 29 of SEQ
            ID NO:2 is Lys or Pro."

( x i ) SEQUENCE DESCRIPTION: SEQ ID NO:2:

```
Phe  Val  Asn  Gln  His  Leu  Cys  Gly  Ser  His  Leu  Val  Glu  Ala  Leu  Tyr
 1                   5                        10                       15

Leu  Val  Cys  Gly  Glu  Arg  Gly  Phe  Phe  Tyr  Thr  Xaa  Xaa  Thr
                20                        25                       30
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Phe  Val  Asn  Gln  His  Leu  Cys  Gly  Ser  His  Leu  Val  Glu  Ala  Leu  Tyr
 1                   5                        10                       15

Leu  Val  Cys  Gly  Glu  Arg  Gly  Phe  Phe  Tyr  Thr
                20                        25
```

( 2 ) INFORMATION FOR SEQ ID NO:4:

( i ) SEQUENCE CHARACTERISTICS:

-continued

```
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Phe  Val  Asn  Gln  His  Leu  Cys  Gly  Ser  His  Leu  Val  Glu  Ala  Leu  Tyr
 1                    5                        10                         15

Leu  Val  Cys  Gly  Glu  Arg  Gly  Phe  Phe  Tyr  Pro  Lys  Thr
                20                        25
```

INSULIN ANALOG FORMULATIONS

FIELD OF INVENTION

The present invention relates to monomeric analogs of human insulin. More specifically, the present invention relates to formulations comprising a monomeric insulin analog and NPH insulin.

BACKGROUND OF THE INVENTION

A wide variety of insulin formulations are currently marketed in order to provide the diabetic patient convenience and flexibility in treating diabetes. The ultimate goal is to achieve near normal glycemic control and thereby minimize the complications associated with diabetes. A number of significant advances have been made in this area including the development of formulations with different pharmacokinetics after subcutaneous injection. These formulations include Regular insulin, semi-Lente insulin, globin insulin, isophane insulin, insulin zinc suspension, protamine zinc insulin, and Ultralente insulin. These formulations can be generally classified as short, intermediate, or long acting.

None of these commercially available insulin formulations alone can provide normal glycemic control for the diabetic patient. Therefore, in addition to dietary control and proper glucose monitoring, a typical treatment regimen requires using a combination of insulin formulations. The most common subcutaneous regimen involves twice-daily injection of mixtures of short and intermediate acting insulin. Galloway, J. A. & Bressler, R., *Med. Clin. North Am.*, 62, 663–680 (1978). Patients routinely prepare mixtures of desired ratios in an extemporaneous fashion by drawing up in a single syringe appropriate volumes from vials of short and intermediate acting insulin. Mixture formulations of short and intermediate acting insulin are currently marketed in a number of fixed ratios. These products offer the patient convenience and better precision over day to day manual mixing.

Mixtures containing a combination of soluble, short acting insulin and a suspension of Neutral Protamine Hagedorn (NPH) are widely marketed because the two formulation types are compatible and have sufficient shelf and in-use stability. JENS BRANGE, GALENICS OF INSULIN (Springer-Verlag 1987). Biphasic preparations, mixtures of crystalline bovine insulin and soluble porcine insulin, have also been prepared. Due to the low solubility of the bovine insulin, these mixtures contain only a small amount of bovine insulin in the soluble phase. Mixed bovine and porcine mixtures of NPH insulin have not been successfully prepared due to physical instability arising from an equilibrium exchange between the dissolved insulin and the solid phase. Id. Other mixtures of short and long acting (Ultralente) formulations cannot be prepared because of significant long-term stability issues arising from incompatibility of the formulations, particularly if a zinc binding buffering agent, such as a phosphate buffer is utilized in the formulation. Most significantly, there are no examples of suspension-type fixed insulin mixture preparations of insulin-NPH and regular insulin currently marketed where two different insulin proteins are combined together.

Most recently, monomeric insulin analogs have been developed that have an ultra rapid time action profile. These monomeric analogs possess a much more rapid onset of activity than regular insulin. The preparation of various monomeric analogs is disclosed in U.S. patent application number 07/388,201 (Chance et al., EPO publication number 383 472), and Brange et al., EPO publication number 214 826. Preparing mixtures containing a rapid-acting insulin analog and NPH insulin is particularly advantageous because the properties of monomeric analogs are considered greatly superior to those of regular insulin. Therefore, mixtures of the monomeric insulin analog and insulin-NPH provide for an immediate reduction in glucose levels and a intermediate acting basal effect.

Unlike regular insulin and insulin-NPH formulation mixtures, mixtures of the monomeric insulin analog and insulin-NPH are heterogeneous. That is, the active protein is different in the NPH crystals and in the solution. In a heterogeneous formulation, any equilibrium exchange that occurs between the non-uniform product i.e., solid and soluble phases, is undesirable. If equilibrium exchange occurs, the heterogeneous formulation fails to maintain the defined ratio of the monomeric insulin in the soluble phase and the insulin in the solid phase over a sufficient shelf-life. That is, if the monomeric analog aggregates with the protamine, the rapid time action would be compromised. Similarly, if the insulin in the solid phase dissolves into the soluble phase, the desired time action profile is altered.

The present invention provides a parenteral formulation comprising a monomeric insulin analog and insulin-NPH. The invention further provides specific conditions under which the formulation is stable for an extended period and, thus suitable for commercial development. The formulations of the present invention permit the diabetic to control more accurately glucose levels thereby delaying or eliminating the onset of various diabetic complications. Quite remarkably, the preferred formulations of the present invention demonstrate extended stability; that is, the equilibrium exchange between the crystalline and soluble proteins is minimized. Accordingly, the formulations are suitable for commercial application.

SUMMARY OF THE INVENTION

This invention provides a parenteral formulation comprising a soluble phase comprising a monomeric insulin analog and a solid phase comprising insulin-NPH crystals. The invention discloses conditions under which the formulation demonstrates extended stability. Accordingly, the invention provides a parenteral pharmaceutical formulation comprising a soluble phase comprising a monomeric insulin analog, and a solid phase comprising insulin-NPH, wherein the insulin-NPH comprises about 0.25 to about 0.30 mg of protamine per 100 U of insulin and the soluble phase contains less than 20% insulin relative to the total soluble protein concentration.

The invention further provides a process for preparing a heterogeneous parenteral formulation, which comprises mixing a monomeric insulin analog and insulin-NPH, wherein the insulin-NPH is aged for at least two days.

DETAILED DESCRIPTION AND PREFERRED EMBODIMENTS

Figure 1:
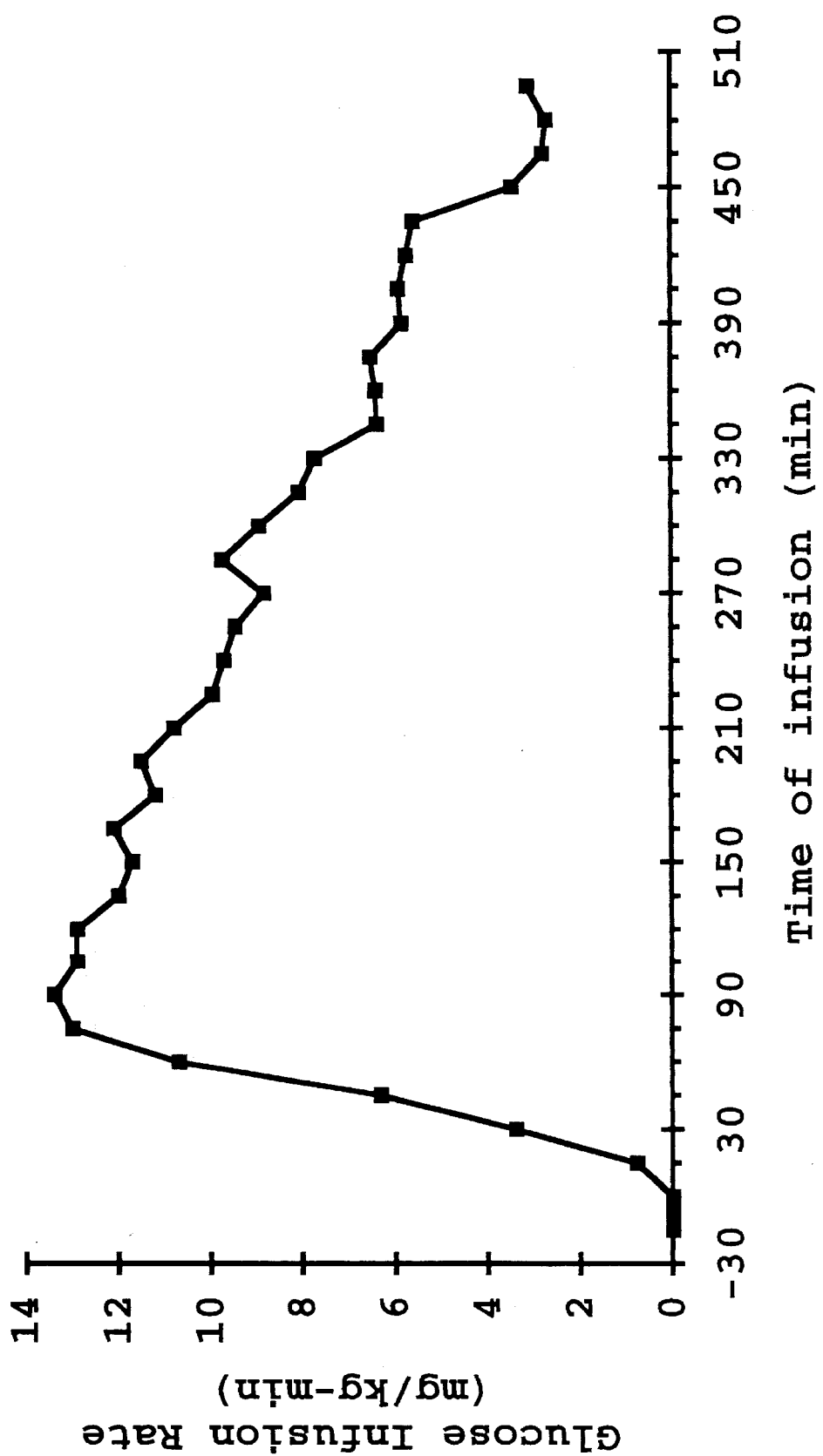
FIG. 1 is a graphical representation of the profile of action of a mixture of $Lys^{B28}Pro^{B29}$-hI and human insulin-NPH. The graph is the mean glucose infusion response rate in a euglycemic clamp study. The figure demonstrates the advantages of the present invention.

All amino acid abbreviations used in this disclosure are those accepted by the United States Patent & Trademark Office as set forth in 37 C.F.R. §1,822(b)(2).

As noted above, the invention provides various formulations of a monomeric insulin analog. The term "monomeric insulin analog" or "insulin analog" as used herein is a fast-acting insulin analog that is less prone to dimerization or self-association. Monomeric insulin analog is human insulin wherein Pro at position B28 is substituted with Asp, Lys, Leu, Val, or Ala, and Lys at position B29 is Lysine or Proline (SEQ ID NO: 1 properly cross-linked to SEQ ID NO: 2); des(B28–B30) (SEQ ID NO: 1 properly cross-linked to SEQ ID NO: 3); or des(B27) (SEQ ID NO: 1 properly cross-linked to SEQ ID NO: 4). Monomeric insulin analogs are described in Chance et al., U.S. patent application No. 07/388,201, (EPO publication number 383 472), and Brange et al., EPO publication 214 826, which are herein incorporated by reference. A particularly preferred monomeric insulin analog is $Lys^{B28}Pro^{B29}$-human insulin (B28 is Lys; B29 is Pro).

One skilled in the art would recognize that other modifications to the monomeric insulin analog are possible. These modifications are widely accepted in the art and include replacement of the histidine residue at position B10 with aspartic acid; replacement of the phenylalanine residue at position B1 with aspartic acid; replacement of the threonine residue at position B30 with alanine; replacement of the serine residue at position B9 with aspartic acid; deletion of amino acids at position B1 alone or in combination with a deletion at position B2; and deletion of threonine from position B30.

The term "insulin" means human insulin, pork insulin, or beef insulin. Preferably, insulin means human insulin.

The term "insulin-NPH" is a suspension of crystalline insulin and protamine. NPH is Neutral Protamine formulation according to Hagedorn. The composition is prepared by techniques widely accepted in the art and described in Krayenbühl and Rosenberg, STENO MEMORIAL HOSPITAL REPORT (COPENHAGEN), 1:60 (1946). The term "insulin-NPH crystals" refers to the crystals of insulin and protamine.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isotonicity agent" refers to an agent that is physiologically tolerated and embarks a suitable tonicity to the formulation to prevent the net flow of water across the cell membrane. Compounds, such as glycerin, are commonly used for such purposes at known concentrations. The concentration of the isotonicity agent in the formulation is in the range known in the art for insulin formulations.

The term "pharmaceutically acceptable preservative" refers to an agent commonly employed to prevent bacterial growth in parenteral formulations. Pharmaceutically acceptable preservatives include phenol, m-cresol, resorcinol, and methyl paraben.

The term "IU" or "U" is international unit.

The term "isophane ratio" is the equilibrium amount of protamine necessary to complex with the analog as taught by Krayenbühl and Rosenberg, STENO MEMORIAL HOSPITAL REPORT (COPENHAGEN), 1:60 (1946). The isophane ratio is determined by titration in a manner well known in the art and described in Krayenbühl, et al.

The term "total soluble protein concentration" means the U/ml of the insulin analog and insulin in the soluble phase.

The term "aged" means holding the insulin-NPH crystals prior to mixing with the monomeric insulin analog. Holding the insulin-NPH crystals allows the crystals to stabilize by aging or maturing.

The present invention provides a heterogeneous mixture formulation of a monomeric analog and insulin-NPH crystals. The invention further provides specific conditions under which the mixture formulations are stable for an extended period; that is, the equilibrium exchange between the solid and soluble phase is minimized. The mixtures provide the rapid onset of action of a monomeric analog and a prolonged action of a insulin-NPH formulation, thus providing optimized control for the diabetic.

The ratio of the monomeric insulin analog to insulin-NPH crystals is from 1:99 to 99:1 on a weight basis. Preferably, the ratio is from 75:25 to 25:75; most preferably from 40:60 to 60:40; and still most preferably, 50:50.

The formulations are prepared by mixing the desired volumes of the components in a standard parenteral formulation diluent. Standard diluents include an isotonicity agent, zinc and a physiologically tolerated buffer. Preferably, the isotonicity agent is glycerin at a concentration of about 16 mg/mL. However, one skilled in the art would recognize that other agents and concentrations are operable. The physiologically tolerated buffer is preferably a phosphate buffer, like dibasic sodium phosphate. Other physiologically tolerated buffers include TRIS, sodium acetate, or sodium citrate. The selection and concentration of buffer is known in the art. Preferably, the concentration is about 3.8 mg/mL. Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts which also might be used in the present invention. Preferably, zinc acetate or zinc chloride is used because these salts do not add new chemical ions to commercially accepted processes.

Preferably, the formulation contains a pharmaceutically acceptable preservative. Pharmaceutically acceptable preservatives include phenol, m-cresol, resorcinol, and methyl paraben. More preferably, the preservative is phenol and m-cresol at a concentration of about 23 mM to 35 mM, most preferably 29 mM. However, the skilled artisan will recognize that many other preservatives are available for use in the present invention.

Early studies leading to the present invention revealed that heterogeneous mixtures of the monomeric analog and insulin-NPH were effective when mixed, but were not suitable for commercial development due to long term instability relating to the equilibrium exchange between the soluble and solid phases.

While extemporaneous mixtures form part of the present invention, the present invention further provides specific conditions which minimize the equilibrium exchange, thus solving the long term stability issue encountered in the early development of the present invention. Accordingly, the present invention further provides heterogeneous mixtures of insulin-NPH crystals and the monomeric analog that are formulated to provide long term stability. Quite surprisingly, under these preferred conditions, the equilibrium exchange between the solid, insulin NPH phase and the soluble, insulin analog phase is minimized and controlled.

The equilibrium exchange is minimized by increasing the maturation time of the insulin-NPH crystals before combining with the soluble analog section and by limiting the amount of protamine used to prepare the insulin-NPH crystals. Therefore, to prepare a stable heterogeneous mixture, the insulin-NPH component must be held for a period prior to mixing. Holding the insulin-NPH allows the crystals to stabilize by aging or maturing. The resulting mixture formulation prepared from stabilized insulin-NPH crystals are less susceptible to the equilibrium exchange when mixed with the monomeric analog. Additional stability is achieved when the insulin-NPH crystals comprise about 0.25 to 0.30 mg of protamine per 100 U of insulin. Most preferably, the protamine concentration is 0.27 mg per 100 U of insulin. When prepared in this manner, the equilibrium exchange expected between the solid and soluble phase is minimized, that is, the soluble phase contains less than 20% insulin, preferably less than 10% insulin relative to the total soluble protein concentration.

Under the conditions described herein, the heterogeneous mixture of a monomeric insulin analog and insulin-NPH is stable. Table 1 and Table 2 demonstrate the insulin-NPH crystal age effect on the resulting formulation. Table 3 measures the extended physical stability of the formulations.

TABLE 3

Physical Stability of Heterogeneous Fixed Mixtures

| Mixture Ratio (NPH/LysPro) | Time at 5° C. (days) | Particle Size (μm) |
|---|---|---|
| 75/25 | 0 | 6.8 |
| 75/25 | 7 | 6.6 |
| 75/25 | 14 | 7.2 |
| 75/25 | 21 | 6.9 |
| 75/25 | 28 | 6.9 |
| 50/50 | 0 | 5.7 |
| 50/50 | 7 | 5.7 |
| 50/50 | 14 | 6.0 |
| 50/50 | 21 | 5.9 |
| 50/50 | 28 | 5.9 |
| 25/75 | 0 | 5.0 |
| 25/75 | 7 | 5.3 |
| 25/75 | 14 | 5.5 |
| 25/75 | 21 | 5.4 |
| 25/75 | 28 | 5.5 |

TABLE 1

Age of NPH Crystals-Initial

| | Mixture Ratio (NPH/LysPro) | NPH Crystal Age (days) | LysPro in soluble phase (U/mL) | Insulin in soluble phase (U/mL) | Insulin in soluble phase (%) |
|---|---|---|---|---|---|
| Protamine 0.30 mg/100 U | 75/25 | 1 | 1.3 | 1.5 | 54. |
| | 75/25 | 3 | 2.7 | 0.5 | 16. |
| | 50/50 | 1 | 24.7 | 5.7 | 19. |
| | 50/50 | 3 | 31.8 | 1.1 | 3. |
| | 25/75 | 1 | 61.6 | 3.5 | 5. |
| | 25/75 | 3 | 65.6 | 1.0 | 2. |
| Protamine 0.27 mg/100 U | 50/50 | 1 | 34.9 | 7.4 | 17.5 |
| | 50/50 | 2 | 38.2 | 4.3 | 10.1 |
| | 50/50 | 3 | 39.4 | 3.0 | 7.1 |
| | 50/50 | 4 | 39.5 | 2.3 | 5.5 |

TABLE 2

Age of NPH Crystals - 3 Month at 5° C.

| | Mixture Ratio | NPH Crystal Age (days) | LysPro in soluble phase (U/mL) | Insulin in soluble phase (U/mL) | Insulin in soluble phase (%) |
|---|---|---|---|---|---|
| Protamine 0.30 mg/100 U | 75/25 | 1 | 1.7 | 0.7 | 29. |
| | 75/25 | 3 | 2.6 | 0.3 | 10. |
| | 50/50 | 1 | 26.1 | 7.7 | 23 |
| | 50/50 | 3 | 30.4 | 3.9 | 11 |
| | 25/75 | 1 | 63.7 | 7.4 | 10 |
| | 25/75 | 3 | 65.8 | 4.3 | 6 |

Only because of the present discovery is it now possible to prepare a stable mixture of insulin-NPH and a monomeric analog formulation, which is suitable for commercialization. The ability to produce a stable, heterogeneous mixture is most unexpected. The ability to minimize the equilibrium exchange between the soluble and solid phases is demonstrated in Tables 1 and 2. Generally, the formulations are considered commercially acceptable if no more than 20% insulin, preferably no more than 10% insulin, relative to the total soluble protein concentration is contained in the soluble phase.

From the data in Tables 1 and 2, one skilled in the art would recognize that the concentration of insulin-NPH and the age of the insulin-NPH crystals are interrelated with regard to stability. That is, at higher insulin-NPH concentrations (e.g., 50:50 to 99:1), the crystals are preferably aged at least two days and most preferably three or more days. Likewise, at the lower insulin-NPH ratios (1:99 to 50:50), the crystals are preferably aged for at least one day and most preferably two or more days.

FIG. 1 demonstrates the biological activity of the present formulations. The formulations combine the rapid action of a monomeric analog and the prolonged action of the insulin-NPH. This activity demonstrates the desired rapid onset coupled with the intermediate basal effect.

The monomeric insulin analogs of the present invention can be prepared by any of a variety of recognized peptide synthesis techniques including classical (solution) methods, solid phase methods, semi synthetic methods, and more recent recombinant DNA methods. For example, Chance et al., U.S. patent application No. 07/388201, EPO publication number 383 472, and Brange et al., EPO 214 826, disclose the preparation of various monomeric analogs.

The following examples are provided merely to further illustrate the invention. The scope of the invention is not construed as merely consisting of the following examples.

EXAMPLE 1

Heterogeneous monomeric analog/NPH mixtures were prepared in desired ratios by mixing 100 IU/mL stock solutions of rapid acting $Lys^{B28}Pro^{B29}$-human insulin analog and human insulin NPH (Humulin-N™). The $Lys^{B28}Pro^{B29}$-human insulin analog stock was prepared by dissolving solid, zinc-containing crystals of the protein in water containing glycerin (16 mg/mL), phenol (0.65 mg/mL) and m-cresol (1.6 mg/mL). The pH was lowered to 1.5–3.0 by the addition of 10% hydrochloric acid. A calculated volume of an acidic ZnO solution (10 mg/mL) was added to supplement the endogenous zinc ion content to 0.7% (0.025 mg/100 IU). This zinc concentration matched that of the suspension, insulin-NPH section. Upon dissolution, the pH was adjusted back to about 7.0 with 10% sodium hydroxide. Sodium phosphate heptahydrate (3.78 mg/mL) was added to the solution. The pH of the solution was adjusted to 7.4. Additional water was added to bring the solution to final volume. The final solution was filtered.

Human insulin-NPH (100 IU/mL) was prepared according to accepted practice as taught by Krayenbühl and Rosenberg (1951). The ideal insulin-NPH suspension contained a fixed protamine ratio of 0.27–0.30 mg/100 U with a zinc concentration of 0.7% (0.025 mg/100 IU). All other excipient concentrations (preservatives and isotonicity agent) were identical to the soluble monomeric analog section. The insulin-NPH crystals were allowed to age in a sealed container at 18°–22° C. for a minimum of 2 days.

EXAMPLE 2

75:25 mixture

To prepare 1 Kg of a 75:25 mixture, 750 g of an aged insulin-NPH section (prepared as previously described) is combined with 250 g of the monomeric analog section (prepared as previously described). The mass of each section is corrected for the specific gravity of each section.

EXAMPLE 3

Time Dependence (stability)

Solutions of $Lys^{B28}Pro^{B29}$-hI were prepared in a diluent system that matched exactly the one used in insulin-NPH. The insulin-NPH used contained a protamine concentration of 0.3 mg/100 U (calculated on a free base basis). Portions of the neutral buffer and acid protein sections from a manufactured lot of vial insulin-NPH were obtained and crystallized in the laboratory. The two sections were then mixed in the desired ratio and the pH adjusted.

Physical stability of the mixtures was evaluated by studying the integrity, size, and shape of the crystals. Particle size was measured using a Coulter Multisizer (Model 646) and Sampling Stand II (Model 999) (Coulter Electronics, Hialeah, Fla.). Sample preparation consisted of resuspending the mixture, withdrawing 0.25 mL, and diluting into 100 mL of a solution of insulin-NPH diluent. Measurements were done with continuous stirring and a sampling time of 50 seconds. Values reported are arithmetic volume mean diameters. The data are demonstrated in Table 3.

EXAMPLE 4

Age of Insulin-NPH Crystal

Preparations of insulin-NPH/$Lys^{B28}Pro^{B29}$-human insulin were prepared in a manner analogous to the above examples. In the formulations prepared, the age of the NPH crystal was varied prior to mixing the insulin NPH from one to four days. For each preparation, the equilibrium exchange was measured by HPLC. HPLC conditions:

Stability was measured using HPLC under the following conditions:

Mobile phase: 0.2M $Na_2SO_4$, pH 2.3:ACN (75:25) with 0.01% TEA

Flow: 1.0 mL/min.

Detector wavelength: 214 nm

Column: Vydac C4

Column Temperature: 40° C.

Injection volume: 20 μL

Samples of human insulin and $Lys^{B28}Pro^{B29}$-human insulin reference standards were reconstituted with 0.01M HCl. The reference standard solutions were mixed in appropriate ratios and diluted with 0.01M HCl. The data are demonstrated in Tables 1 and 2.

EXAMPLE 5

Analysis of 70:30 insulin-NPH to $Lys^{B28}Pro^{B29}$-human insulin

The study was performed in a conscious dog model. Prior to the commencement, three basal samples were taken. An infusion of somatostatin (0.3 μg/Kg-min.) was initiated. After a 10 minute interval, a subcutaneous injection of a 70:30 mixture of insulin-NPH and $Lys^{B28}Pro^{B29}$-human insulin was administered. Frequent monitoring of plasma glucose was also initiated and a variable glucose (20%) infusion was given so as to maintain near-normal glycemia. Samples were taken throughout and were analyzed for immunoreactive insulin (Linco antibody) and glucose. The concentration of a 70:30 mixture of insulin-NPH and $Lys^{B28}Pro^{B29}$-human insulin rise very rapidly to levels of near 90 μU/ml and then decay slowly to 10–15 μU/ml at 500 minutes. The data are demonstrated in FIG. 1.

We claim:

1. A parenteral pharmaceutical formulation comprising a soluble phase comprising an insulin analog and a solid phase comprising insulin-NPH crystals; wherein: the insulin analog is human insulin wherein Pro at position B28 is substituted with Asp, Lys, Leu, Val, or Ala, and Lys at position B29 is Lysine or Proline, des(B28–B30), or des(B27); the insulin-NPH crystals comprise about 0.25 to about 0.30 mg of protamine per 100 U of insulin; and the soluble phase contains less than about 20% insulin relative to the total soluble protein concentration.

2. The formulation of claim 1, wherein the soluble phase contains less than 10% insulin relative to the total soluble protein concentration.

3. The formulation of claim 2 wherein the insulin-NPH crystals comprise about 0.27 mg of protamine per 100 U of human insulin.

4. The formulation of claim 3 wherein the ratio of insulin analog to insulin-NPH crystals is about 1:99 to 99:1.

5. The formulation of claim 4 wherein the insulin analog is $Lys^{B28}Pro^{B29}$-human insulin.

6. The formulation of claim 5 wherein the ratio of $Lys^{B28}Pro^{B29}$-human insulin to insulin-NPH is about 75:25 to 25:75.

7. The formulation of claim 6 wherein the ratio of $Lys^{B28}Pro^{B29}$-human insulin to insulin-NPH is about 50:50.

8. The formulation of claim 7 which further comprises a pharmaceutically acceptable preservative.

9. The formulation of claim 8 wherein the preservative is phenol, m-cresol, or a mixture thereof.

10. The formulation of claim 9 which further comprises an isotonicity agent.

11. A process for preparing a heterogeneous parenteral formulation, which comprises mixing a soluble phase comprising an insulin analog, and a solid phase comprising insulin-NPH wherein the insulin analog is human insulin wherein Pro at position B28 is substituted with Asp, Lys, Leu, Val, or Ala, and Lys at position B29 is Lysine or Proline, des(B28–B30), or des(B27); and the formulation contains less than 20% insulin relative to the total soluble protein concentration in the soluble phase.

12. The process of claim 11, wherein the insulin-NPH comprises about 0.25 to about 0.30 mg of protamine per 100 U of insulin; and the insulin-NPH is aged for at least two days.

13. The process of claim 12, wherein the soluble phase contains less than 10% insulin relative to the total soluble protein concentration.

14. The process of claim 13, wherein the insulin analog is $Lys^{B28}Pro^{B29}$-human insulin.

15. An insulin formulation produced by the process of claim 14.

* * * * *